US012099634B2

(12) United States Patent
Rosenberg et al.

(10) Patent No.: US 12,099,634 B2
(45) Date of Patent: *Sep. 24, 2024

(54) SYSTEMS AND METHODS FOR A DE-IDENTIFIED MEDICAL AND HEALTHCARE DATA MARKETPLACE

(71) Applicant: MEDICOM TECHNOLOGIES INC., Raleigh, NC (US)

(72) Inventors: Michael Rosenberg, Raleigh, NC (US); Malcolm Benitz, Raleigh, NC (US); Jason Suttles, Raleigh, NC (US); Chris Woodlief, Raleigh, NC (US); Brent Goldstein, Raleigh, NC (US)

(73) Assignee: Medicom Technologies, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/102,743

(22) Filed: Jan. 29, 2023

(65) Prior Publication Data

US 2023/0169211 A1 Jun. 1, 2023

Related U.S. Application Data

(63) Continuation of application No. 17/866,755, filed on Jul. 18, 2022, now Pat. No. 11,593,522, which is a continuation of application No. 17/589,805, filed on Jan. 31, 2022, now Pat. No. 11,423,176, which is a continuation of application No. 17/029,221, filed on Sep. 23, 2020, now Pat. No. 11,270,027, which is a continuation of application No. 16/674,120, filed on Nov. 5, 2019, now Pat. No. 10,817,622.

(60) Provisional application No. 62/756,132, filed on Nov. 6, 2018.

(51) Int. Cl.
*G06F 21/62* (2013.01)
*G16H 15/00* (2018.01)
*G16H 30/20* (2018.01)
*G16H 30/40* (2018.01)
*H04L 9/40* (2022.01)

(52) U.S. Cl.
CPC ......... *G06F 21/6254* (2013.01); *G16H 15/00* (2018.01); *G16H 30/20* (2018.01); *G16H 30/40* (2018.01); *H04L 63/0428* (2013.01)

(58) Field of Classification Search
CPC .... G06F 21/6254; G16H 30/40; G16H 15/00; G16H 30/20; H04L 63/0428
See application file for complete search history.

(56) References Cited

U.S. PATENT DOCUMENTS

| | | | | |
|---|---|---|---|---|
| 10,347,293 B1* | 7/2019 | Skinner | ................ | G11B 27/031 |
| 2005/0236474 A1* | 10/2005 | Onuma | .................. | G06Q 10/10 |
| | | | | 235/382 |
| 2011/0150334 A1* | 6/2011 | Du | ........................ | G06V 40/19 |
| | | | | 382/173 |
| 2016/0307063 A1* | 10/2016 | Bright | .................... | G16H 30/40 |

(Continued)

*Primary Examiner* — Mohammed Waliullah

(57) ABSTRACT

The invention relates generally to systems and methods for protecting patient privacy when health care information is shared between various entities and, in particular, to systems and methods that implement a multi-stage sanitizing routine for de-identifying patient data from medical reports and diagnostic images to ensure patient privacy, while preserving the ability for sanitized medical reports and diagnostic images to be re-identified.

18 Claims, 12 Drawing Sheets

(56) References Cited

U.S. PATENT DOCUMENTS

2018/0276248 A1\* 9/2018 Burkett .................. G06F 16/54
2019/0019300 A1\* 1/2019 Simpson ................ G16H 30/20

\* cited by examiner

| Tag ID | Tag Name | Tag ID | Tag Name |
|---|---|---|---|
| 80,020 | StudyDate | 81,060 | NameOfPhysicianReadingStudy |
| 80,021 | SeriesDate | 81,062 | PhysicianReadingStudyIDSequence |
| 80,022 | AcquisitionDate | 81,070 | OperatorsName |
| 80,023 | ContentDate | 100,010 | PatientsName |
| 80,024 | OverlayDate | 100,020 | PatientID |
| 80,025 | CurveDate | 100,021 | IssuerOfPatientID |
| 0008,002A | AcquisitionDatetime | 100,030 | PatientsBirthDate |
| 80,030 | StudyTime | 100,032 | PatientsBirthTime |
| 80,031 | SeriesTime | 100,040 | PatientsSex |
| 80,032 | AcquisitionTime | 101,000 | OtherPatientIDs |
| 80,033 | ContentTime | 101,001 | OtherPatientNames |
| 80,034 | OverlayTime | 101,005 | PatientsBirthName |
| 80,035 | CurveTime | 101,010 | PatientsAge |
| 80,050 | AccessionNumber | 101,040 | PatientsAddress |
| 80,080 | InstitutionName | 101,060 | PatientsMothersBirthName |
| 80,081 | InstitutionAddress | 102,150 | CountryOfResidence |
| 80,090 | ReferringPhysiciansName | 102,152 | RegionOfResidence |
| 80,092 | ReferringPhysiciansAddress | 102,154 | PatientsTelephoneNumbers |
| 80,094 | ReferringPhysiciansTelephoneNumber | 200,010 | StudyID |
| 80,096 | ReferringPhysicianIDSequence | 380,300 | CurrentPatientLocation |
| 81,040 | InstitutionalDepartmentName | 380,400 | PatientsInstitutionResidence |
| 81,048 | PhysicianOfRecord | 0040,A120 | DateTime |
| 81,049 | PhysicianOfRecordIDSequence | 0040,A121 | Date |
| 81,050 | PerformingPhysiciansName | 0040,A122 | Time |
| 81,052 | PerformingPhysicianIDSequence | 0040,A123 | PersonName |

FIG. 9

SYSTEMS AND METHODS FOR A DE-IDENTIFIED MEDICAL AND HEALTHCARE DATA MARKETPLACE

CROSS-REFERENCE TO RELATED APPLICATION

This application claims the benefit of U.S. Provisional Patent Applications No. 62/756,132 entitled "SYSTEM AND METHOD FOR DE-IDENTIFYING DATA" filed on Nov. 6, 2018 which is commonly owned, the disclosure of which is incorporated herein by reference in its entirety.

BACKGROUND

Field of the Invention

The present invention relates, in general, to systems and methods for protecting patient privacy when health care and medical information is shared between various entities and, in particular, to systems and methods that implement a multi-stage sanitizing routine for de-identifying protected health information (PHI) from medical and healthcare data, such as, for example, medical reports and diagnostic images, in order to ensure patient privacy, while preserving the ability for sanitized medical reports and diagnostic images to be re-identified.

Description of Related Art

The ease with which electronic data can be transmitted, together with the increasing use of health care, medical, and patient information (collectively, "medical information") for research purposes, has raised concerns about patient confidentiality and institutional liability, as well as concerns surrounding the protection of patient privacy when such medical information is transmitted between various entities, such as, for example, a medical provider and a research institution.

To maintain patient privacy in the context of research and various third-party uses, it must be ensured that any medical information used in aggregate is not associated with any specific patient or individual, and that only authorized entities based on a patient's informed consent have access to such medical data.

Such patient privacy can be maintained by disclosing only specific portions of the medical information through de-identification processes, where portions of the medical information that may be classified as personally identifiable information (PII). PII can be any data that could potentially identify a specific patient or individual. Sensitive PII is information which, when disclosed, could result in harm to an individual whose privacy has been breached. Sensitive PII can include biometric information, medical information, personally identifiable financial information, and unique identifiers such as passport or Social Security numbers. PHI and PII is typically removed, deleted, masked, or replaced with non-identifiable information through such conventional de-identification processes.

In the United States, standards such as Health Insurance Portability and Accountability Act (HIPAA) have resulted in federal regulations that place strict requirements on the archiving and disclosure of medical information. For example, in accordance with HIPAA, federal regulations have been enacted that require healthcare organizations, physicians, and entities having access to such medical information to ensure the protection, privacy and security of the patient information, which can include PHI and PII. In particular, the "Privacy Rule" of HIPAA provides federal privacy regulations that set forth requirements for confidentiality and privacy policies and procedures, consents, authorizations and notices, which must be adopted in order to maintain, use, or disclose PHI and PII in the course of a patient's treatment, as well as other business functions or other activities.

The HIPAA Privacy Rule allows for entities to de-identify PHI for certain purposes so that medical information may be used and disclosed freely, without being subject to the protections afforded by the Privacy Rule. The term "de-identified data" as used by HIPAA refers to medical information from which all information, data and tags that could reasonably be used to identify the patient has been removed (such as, for example, their name, address, social security number, date of birth, contact information, and the like).

Conventional methods for de-identifying medical data include simply stripping all information considered to be PHI or PII from a medical record that can be used to determine the identity of a patient, or replacing such information with something else (such as, for example, replacing the actual patient name with the string "name"). Although the medical records are de-identified with such conventional methods, there remains no mechanism by which PHI or PII can be recovered for re-identification purposes, if required.

In addition, various methods of de-identification generally of documents and metadata fields include built-in code to remove portions marked for de-identification, or utilize template-based approaches to redact information from documents. Methods of de-identification have been used for text documents, structured metadata fields such as in Digital Imaging and Communications in Medicine (DICOM) metadata, but de-identification of visual media data when the medical information is burned into, or embedded inside the media, can be difficult and time consuming.

Therefore, there is a need for a reliable system and method to ensure complete de-sanitization of both diagnostic images and associated medical reports containing text and burned in medical information, whereby the sanitized PHI and PII can be recovered for re-identification purposes.

SUMMARY

In one embodiment, the invention relates to a method for de-identifying medical data, comprising: receiving, at a server, a selection of at least one medical record to be de-identified of patient information, wherein the medical record includes a diagnostic image and a medical report; determining, by the server, a modality associated with the diagnostic image; retrieving, by the server, a de-identification profile for the modality, wherein the de-identification profile specifies at least one area of the diagnostic image that contains patient information; applying, by a sanitizing engine coupled to the server, a blackout zone over the area of the diagnostic image specified in the de-identification profile, wherein the blackout zone prevents the patient information in the area from being visible; performing, by the sanitizing engine, an optical character recognition operation in the area after the blackout zone has been applied; determining, by the sanitizing engine, if any characters are detected in the area after the blackout zone has been applied; detecting, by the sanitizing engine, a boundary for a region of interest of the diagnostic image if no characters are detected in the area after the blackout zone has been applied; detecting, by the sanitizing engine, if non-black pixels are present outside of the boundary for the region of interest;

and performing a first operation by the sanitizing engine to convert any non-black pixels detected outside of the boundary for the region of interest to black pixels, or performing a second operation by the sanitizing engine to encapsulate the diagnostic image into a DICOM format if non-black pixels are not detected outside of the boundary for the region of interest.

In another embodiment, the invention relates to a method for de-identifying medical data, comprising: receiving, at a server, a selection of at least one medical record to be de-identified of patient information, wherein the medical record includes a diagnostic image and a medical report; applying, by a sanitizing engine coupled to the server, a sanitizing process in an area of the diagnostic image determined by a pre-stored de-identification profile, wherein the de-identification profile specifies the area of the diagnostic image containing patient information, and wherein the sanitizing process prevents the patient information in the area from being visible; detecting, by the sanitizing engine, if any characters are present in the area after the sanitizing process has been applied; detecting, by the sanitizing engine, a gradient boundary for a region of interest of the diagnostic image if no characters are detected in the area after the sanitizing process has been applied; and converting, by the sanitizing engine, any non-black pixels detected outside of the gradient boundary to black pixels.

In another embodiment, the invention relates to a system for de-identifying medical data, comprising: a database configured to store at least one medical record, wherein the medical record includes a diagnostic image and a medical report; a sanitizing engine communicatively coupled to the database, the sanitizing engine configured to import the medical record from the database, the sanitizing engine further configured to apply a blackout zone in an area of the diagnostic report to that contains patient information, the sanitizing engine further configured to detect if characters exist in the area that the blackout zone was applied, the sanitizing engine further configured to detect a gradient boundary for a region of interest on the diagnostic image, and the sanitizing engine further convert non-black pixels that exist outside of the gradient boundary to black pixels; the sanitizing engine further configured to encapsulate the diagnostic image into a DICOM file; and a server communicatively coupled to the database and the sanitizing engine, the server configured to transmit the DICOM file to a remote computing system.

BRIEF DESCRIPTION OF THE DRAWINGS

These and other embodiments of the disclosure will be discussed with reference to the following exemplary and non-limiting illustrations, in which like elements are numbered similarly, and where:

FIG. 9 is a table with exemplary DICOM metadata, according to an embodiment of the invention.

DEFINITIONS

The following definitions are meant to aid in the description and understanding of the defined terms in the context of the present invention. The definitions are not meant to limit these terms to less than is described throughout this application. Such definitions are meant to encompass grammatical equivalents.

As used herein, the term "medical data" can refer to, for example, health and healthcare related data, patient data, electronic medical records, medical imaging studies, medical and diagnostic images, diagnostic reports, fitness and activity data, medical reports, and the like.

As used herein, the term "medical reports" can refer to, for example, any patient data, patient charts, diagnostic notes, opinions, reads and reports, medical test and laboratory results, surgical history, family history, medications, medical allergies, social history, habits (such as, for example, drug, tobacco and alcohol use), immunization history, clinical information, growth and development history, medical encounters, physical examination observations, progress notes, and the like.

As used herein, the term "recipient" can refer to, for example, medical clinics, hospitals, medical providers, health insurance providers, diagnostic sites, imaging sites, data customers, and the like. A "recipient" can further refer to entity or individual that analyzes, processes, compiles, or otherwise utilizes aggregate medical and health-related data for research, analytics, advertising, marketing, monetization, or reporting purposes. The recipient can be an academic institution, a government research laboratory, a non-profit entity, or a for-profit entity, such as a pharmaceutical, health insurance, biotechnology, wearable device, physiological monitoring, or medical device company.

As used herein, the term "PHI" can refer not only protected health information, but also to PII and any other information that may be consider private, confidential, personally identifying, financial information, and the like.

DETAILED DESCRIPTION

It should be understood that aspects of the invention are described herein with reference to the figures, which show illustrative embodiments. The illustrative embodiments herein are not necessarily intended to show all embodiments in accordance with the invention, but rather are used to describe a few illustrative embodiments. Thus, aspects of the invention are not intended to be construed narrowly in view of the illustrative embodiments. In addition, although the invention is described with respect to its application for the transfer of medical information containing DICOM data applications, it is understood that the system could be implemented in any setting where the transfer of any type or form of medical or patient data may be useful.

Figure 1:
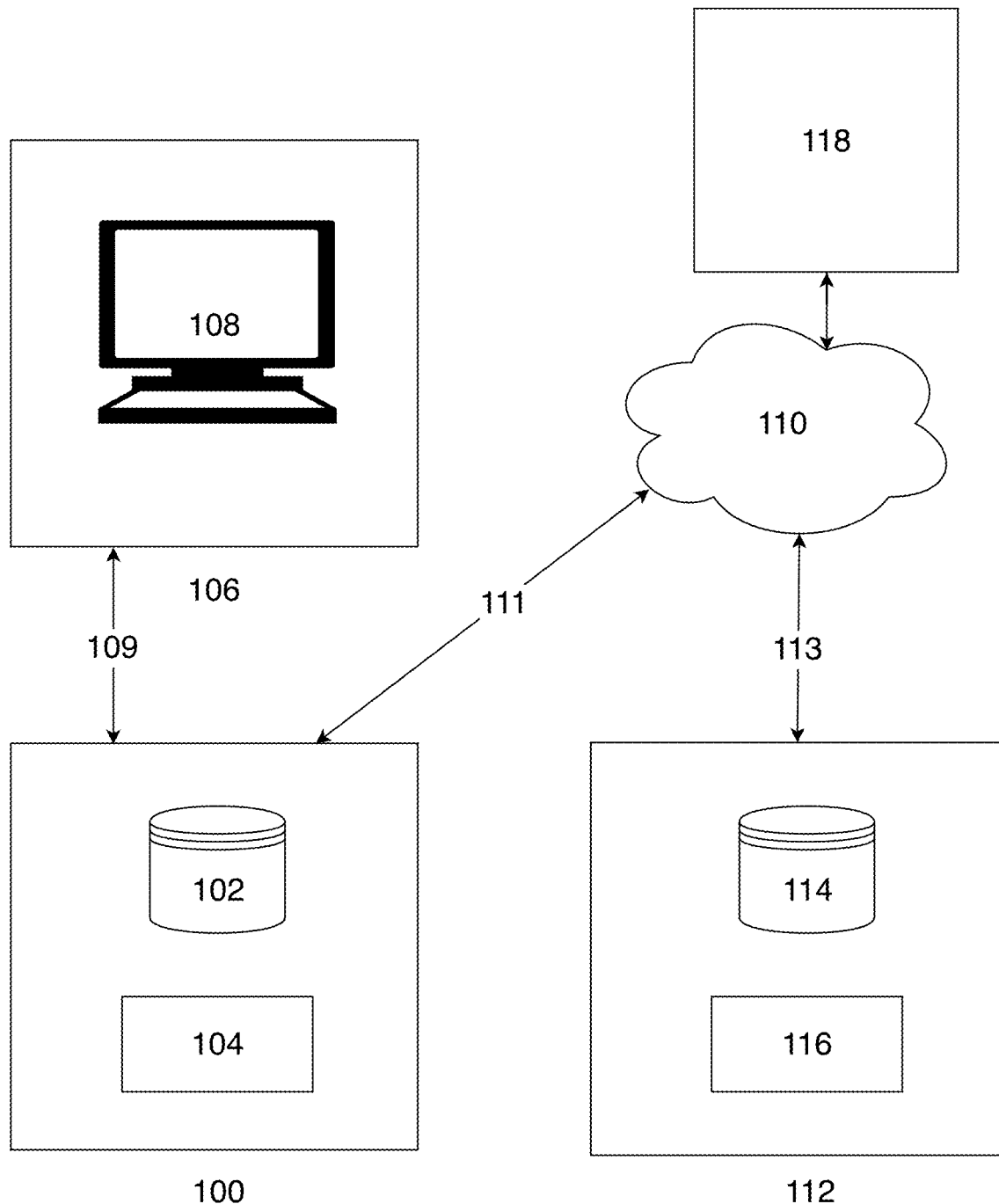
FIG. 1 is a network architecture diagram of a system for de-identifying medical data, according to an embodiment of the invention.

FIG. 1 is a network architecture diagram of a system for de-identifying medical data, according to an embodiment to the invention. The system includes a data provider 100 that is communicatively coupled to an institution 106, such as a medical facility, hospital, health care provider, diagnostic imaging center, diagnostic imaging station, and the like. In an embodiment, the institution 106 can include a picture archiving and communication system (PACS) 108 via a communication link 109. The data provider 100 can be remote from the PACS 108, and the data provider 100 can be communicatively coupled to multiple local or distributed PACS (not shown).

In an embodiment, the data provider 100 is operated by a third-party not affiliated with, or owned or operated by, the institution 106. The data provider 100 facilitates the transfer of de-identified medical data between the PACS 108 and various third-party recipients 112. The data provider 100 can facilitate an encrypted direct peer-to-peer communication channel for securely transferring medical data between the PACS 108 and/or database 102 and such third-party recipients 112, where the PACS 108 and/or database 102 are not within a data transfer network utilized by a recipient 112. The encrypted direct peer-to-peer communication channel is described in more detail in commonly owned application Ser. No. 16/281,409, entitled, METHODS AND SYSTEMS FOR TRANSFERRING SECURE DATA AND FACILITATING NEW CLIENT ACQUISITIONS, the contents of which are hereby incorporated by reference in its entirety.

In an embodiment, the data provider 100 can include computing hardware and software, such as a database 102 and sanitizing engine 104. In another embodiment, the database 102 and/or sanitizing engine 104 can be cloud-based, and located remotely from the data provider 100, such as on a remote server provided by Amazon Web Services® or the like. In an embodiment, the data provider 100 is configured as a server, virtual server, or a distributed server can store data, as well as execute programs, algorithms, scripts, and applications.

The data provider 100 is communicatively coupled to a network 110 via a communication link 111, where the network 110 in turn is communicatively coupled to a recipient 112 via communication link 113.

In an embodiment, the recipient 112 can be a customer that purchases de-identified medical data. The recipient 112 can purchase de-identified medical data in bulk, with specific criteria, or in bulk. The cost of such de-identified medical data can be based on the number of medical data requested, the modality of medical data requested, the extent of sanitizing required, and/or custom sanitizing requirements.

In an embodiment, the recipient 112 can also include a database 114, and a virtual machine 116, where the virtual machine 116 is a software instance that is operated, provided, or developed by the data provider.

As described herein the, databases 102 and 114 can be centralized and stored on respective servers, or can be distributed databases. In an embodiment, the databases 102 and 114 can be relational databases, or can leverage blockchain technology.

The communication links 109, 111 and 113 may be any type of communication links suitable to allow interaction between the data provider 100 and PACS 108, the data provider 100 and recipient 112, as well as with the network 110. For example, the communication links 109, 111 and 113 may each be a wired network, a wireless network, or any combination thereof. Further, communication links 109, 111 and 113 may include a distributed computing network, an intranet, a local-area network (LAN) and/or a wide-area network (WAN), or any combination thereof. For example, the LAN may make use of WIFI in its many variations and the WAN may make use of broadband, cellular and/or satellite networks using technologies including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies. However, those of ordinary skill in the art will appreciate that the communication links 109, 111 and 113 are not limited thereto. In another embodiment, the communication links 109, 111 and 113 may each include ethernet, Firewire, parallel, serial, or USB connections, or short-range communication protocols such as Bluetooth, infrared, Zigbee, and the like.

In an embodiment, a medical data marketplace 118 can be communicatively coupled to the network 110. The medical data marketplace 118 can allow sellers, such as data providers, institutions, medical service providers, hospitals, medical clinics, and/or individual patients to offer de-identified medical data for sale or license to various third-party customers.

In an embodiment, the medical data marketplace 118 can allow customers to search for, and purchase, medical data based on specific criteria. The criteria can include, for example, modality type, equipment manufacturer, body part, a study description, protocol name, a requested procedure description, a scheduled procedure step description, and/or a keyword or Boolean search. In an embodiment, the query can include one or more criteria, and can further include a study date or study date range. The criteria can further include a geographic criteria, such as a town, city, state, country, or geographic region, as well as a demographic criteria, such as a patient race, a patient age, and patient sex. In an embodiment, customers can further search for medical data based on a defined metadata tag.

In an embodiment, customers may also purchase medical data in bulk, such as random lots, or lots matching at least one criteria. In an embodiment, the data provider 100 can operate, own, or manage the medical data marketplace 118, and the data provider 100 can receive a commission from each medical data transaction that occurs on the medical data marketplace 118, with the seller also receiving a portion of the proceeds from the transaction with the customer. In addition, the data provider 100 can also receive a listing fee from sellers, as well as a membership fee from customers.

In another embodiment, the medical data marketplace 118 can offer auctions on medical data. The medical data marketplace 118 can further utilize blockchain technology to provide anonymity, privacy, and security for both sellers and customers.

In yet another embodiment, each of the sellers participating on the medical data marketplace 118 can collectively or cooperatively share the proceeds that are generated from transactions on the medical data marketplace 118. In an embodiment, each seller can receive an equal amount of the proceeds. In another embodiment, each seller can receive a pro-rata amount of the proceeds based on the percentage of data contributed by each seller relative to the total amount of data on the marketplace.

Figure 2:
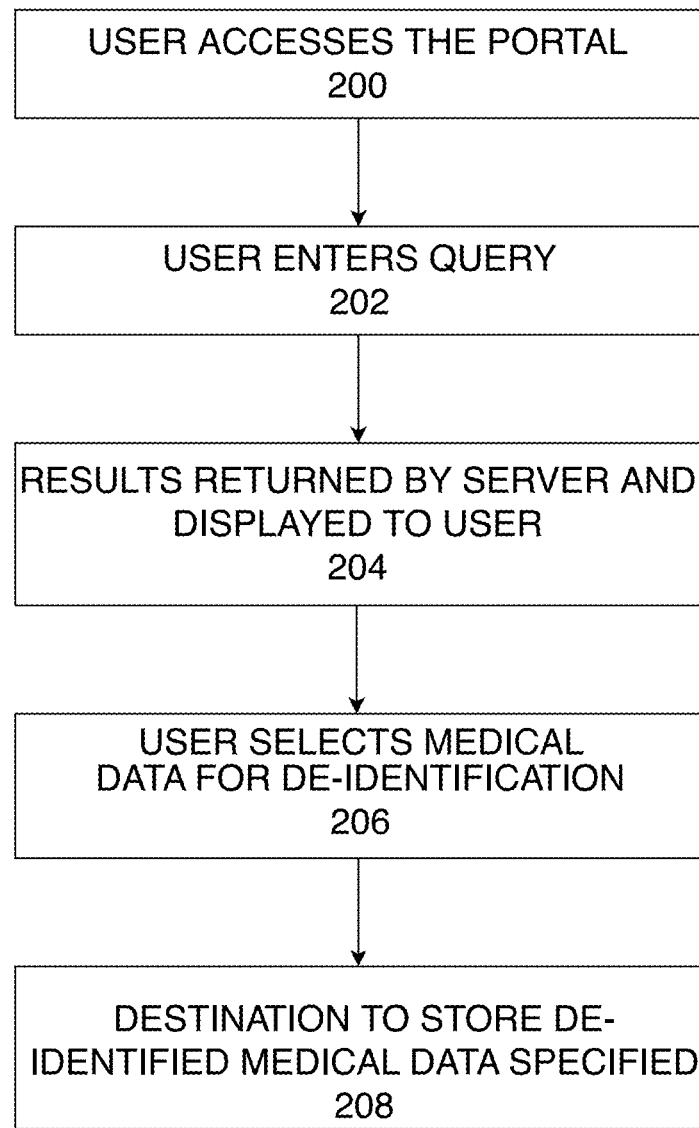
FIG. 2 is a flowchart illustrating the steps of selecting medical data for de-identification, according to an embodiment of the invention.

FIG. 2 is a flowchart illustrating the steps of selecting medical data for de-identification, according to an embodiment of the invention. In an embodiment, at step 200, a user can access a portal, such as a secure web site via a Uniform Resource Location (URL) using a browser on a computing device. The portal can be stored on or executed from, for example, the data provider 100, and the portal allows the user to retrieve medical data stored on the database 102.

In an embodiment, prior to being able to access the portal, the user must enter credentials, such as a login and password, or other indicia that verifies their identity. The credentials can include user's mobile device number, login, password, email address, phone number, account number, personal identification number (PIN), name, driver's license number, social security number, birthdate, employee number, and/or a unique account identification code previously provided to the user by an authorizing entity, such as an employer or data provider. In another embodiment, the credentials can be biometric, such as a fingerprint, iris, facial, or voice scan. In yet another embodiment, the credential can be a gesture input by the user, such as a on a touchscreen or touchpad.

In an embodiment, the user is external to, and not affiliated with, the data provider 100, but rather affiliated with the recipient 112. The recipient 112 and the data provider 100 can have a business arrangement or contractual agreement in place that allows the user to access the database 102 via the portal. In this embodiment, the user may access the portal via the virtual machine 116 located at the recipient 112 which is communicatively coupled to the data provider 100.

In another embodiment, the user can access the portal directly via their PACS, such as PACS 108 or a PACS located at, or operated by, the recipient 112.

At step 202, the user can enter a query by selecting from various criteria, such as, for example, modality type, equipment manufacturer, body part, a study description, protocol name, a requested procedure description, a scheduled procedure step description, and/or a keyword or Boolean search. In an embodiment, the query can include one or more criteria, and can further include a study date or study date range. The query can further include a geographic criteria, such as a town, city, state, country, or geographic region, as well as a demographic criteria, such as a patient race, a patient age, and patient sex. In an embodiment, the user can perform a query based on a defined metadata tag.

In another embodiment, the query can include a medical condition or ailment, such as, for example, brain tumors, cancers, traumatic brain injury, developmental anomalies, multiple sclerosis, stroke, dementia, infection, fractures, bone bruises, etc.

At step 204, the query results are displayed to the user. The query results can be matching medical data that are returned to the user, where the medical data information displayed does not include any PHI. For example, the user may only be shown the patient age, sex, and criteria that matches the query from each matching medical data. In this embodiment, the medical data are not yet sanitized; however, the user may only view non-PHI details in order to select medical data for de-identification. In an embodiment, the data provider 100 utilizes Structured Query Language (SQL) to retrieve the query results from the database 102. In another embodiment, the data provider 100 can utilize various relational alternatives to SQL, as well as alternatives that utilize search frameworks for non-relational database models.

At step 206, the user can select the desired medical data to de-identify. In an embodiment, the medical data consists of diagnostic studies which include diagnostic images, such as radiology images, as well as diagnostic reads, interpretation, clinical information, notes or reports related to those diagnostic images.

The user can manually select individual medical data to de-identify, or can select all medical data in the query results. In another embodiment, the user can filter the query results to obtain a narrower result set. For example, if the user initially queried for all medical data for "males" and "brain tumor", the user can filter the results further by, for example, an age range, a geographic filter, a modality type, and the like. The user can then automatically select medical data to de-identify based on the results of a subsequent filtering operation, for example, such as all medical data from a male patient, or all medical data from patients under the age of 60, etc.

At step 208, the user can select a destination to store or transmit the de-identified medical data to. In an embodiment, if the user is external to the data provider 100, then the destination can only be affiliated with the recipient 112. If the user is internal to the data provider 100, or institution 106 being serviced by the data provider 100, then the user can select a specific internal or external destination.

In another embodiment, the de-identified medical data can be automatically routed to a pre-specified or pre-determined destination. For example, the de-identified medical data can be routed based on pre-defined routing rules, a pre-defined destination based on the user's profile, a pre-defined destination based on the recipient 112, or based on a previously utilized destination by the user.

In another embodiment, the pre-defined destination can be determined by the institution 106 or the data provider 100. For example, the institution 106 or the data provider 100 may only allow certain destinations to receive de-sanitized medical data, and the user may be limited to selecting from a pre-defined list of destinations, or may be limited to an automatically selected destination whereby the user does not have the ability to modify, select, or change the destination.

Figure 3:
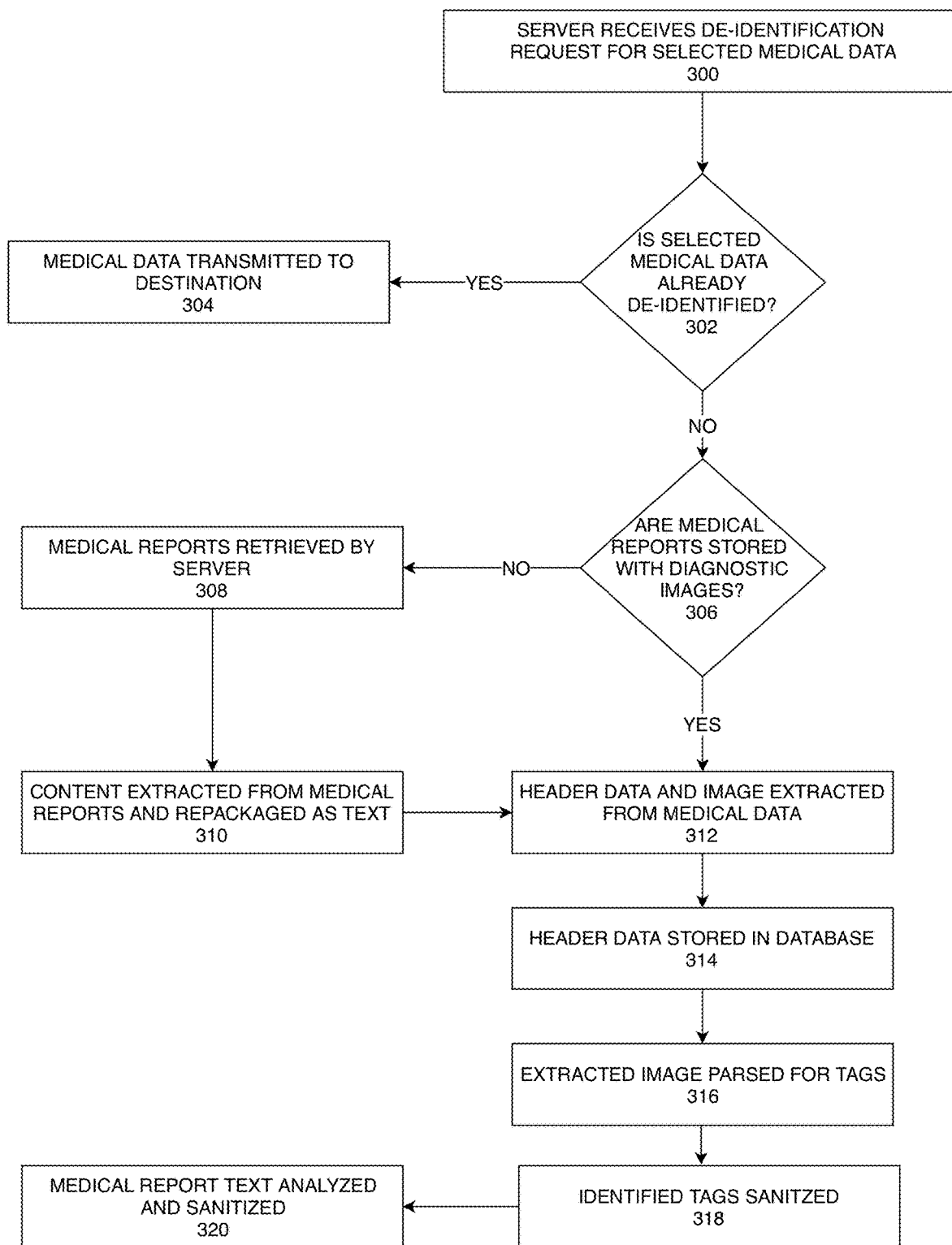
FIG. 3 is a flowchart illustrating the steps of de-identifying DICOM metadata and medical reports, according to an embodiment of the invention.

FIG. 3 is a flowchart illustrating the steps of de-identifying DICOM metadata and medical reports, according to an embodiment of the invention. At step 300, the data provider 100 and/or the sanitizing engine 104 receives the request to de-identify the medical data selected by the user at step 206. The selected medical data are imported into the sanitizing engine 104 from the database 102. At step 302, the sanitizing engine 104 determines if a selected medical data has previously been de-identified. If the selected medical data has previously been de-identified, then at step 304, the de-identified medical data is retrieved from the database 102, or from another database communicatively coupled to the data provider 100, and the de-identified medical record is transmitted to the destination specified at step 208.

In an embodiment, the destination is a network or electronic address for the virtual machine 116, where the virtual machine 116 is configured to receive the de-identified medical data.

If the selected medical data has not been previously de-identified, then at step 306, the sanitizing engine 104 determines if associated medical reports are stored with the diagnostic images in the medical data, such as images obtained via medical imaging modalities such as digital X-ray, Computed Tomography (CT), computed radiography, Magnetic Resonance Imaging (MM), Positron Emission Tomography (PET), thermoacoustic imaging, film-based optical imaging, ultrasound imaging, and nuclear medicine-based imaging.

In an embodiment, the diagnostic images can be DICOM encapsulated files that contain a document, such as a PDF document, that have been encapsulated with a DICOM information object and/or DICOM image(s).

If associated medical reports are not stored with diagnostic images within the medical data, then at step 308, the data provider 100 retrieves the associated medical reports from a corresponding storage location. In an embodiment, the corresponding storage location can be a database on the data provider 100, such as database 102, or can be located on the PACS 108, another server, distributed server system, data storage facility, or provided by another data provider.

At step 310, the sanitizing engine 104 extracts content from the associated medical reports, and packages the extracted content as medical report text. The process then continues to step 312, as is described in more detail below.

If the sanitizing engine 104 determines that associated medical reports are stored with the diagnostic images in step 306, then the process continues to step 312 where header data and image data are extracted from the DICOM encapsulated file. In an embodiment, the sanitizing engine 104 extracts the DICOM image into a JPEG image, and extracts the header data into a parseable document, such as a document in an XML, JSON, YAML, AXON, ConfigObj, OGDL, HDF, SSYN, SDL, Boulder, ONX, SMEL, Groovy-Markup, ATerms, LNML, GODDAG, JITTs, UBF format, and the like.

At step 314, the header data and the parseable document are copied and stored into a database 114, such as database 114 affiliated with recipient 112. In an embodiment, the header data and the parseable document can be stored with the addition of a private tag field containing a randomly generated key to be used for re-identification purposes. However, the private tag field may not be mandatory. In an embodiment, the randomly generated key is not used to decrypt the database 114. In an embodiment, the database 114 can be encrypted, or alternatively, the header data and the parseable document are stored in an encrypted fashion. In an embodiment, step 314 is an optional step, and executed only if the data provider 100 or institution 106 has enabled, requested, or allowed for re-identification of the medical data. In an embodiment, the header data and/or parseable document is associated with a unique identification string, such as a number, characters, alpha-numeric sequence, and the like, when stored into the database 114, where the unique identification string is used for re-identification.

In an embodiment, the unique identification string is a SOP instance unique identification (SOP instance UID). In an embodiment, the unique identification string is generated using a hexadecimal salt hashing mechanism, such that the unique identification string has no relation to the underlying patient, patient data, PHI, PII, or information that existed in the header data, parseable document, or medical data prior to the de-identification process.

In an embodiment, the unique identification string is stored in a dedicated database, such as database 114 maintained by the recipient 112. In another embodiment, the unique identification string is stored in a dedicated database that is maintained by the institution 106, the data provider 100, the recipient 112, or a covered entity that is associated with the user, and which is configured to receive the de-identified medical data. In another embodiment, the dedicated database can be local to the user, the recipient 112, or the institution 106, can be located on the data provider 100, or can be located on another server, distributed server system, or data storage facility.

Figure 10:
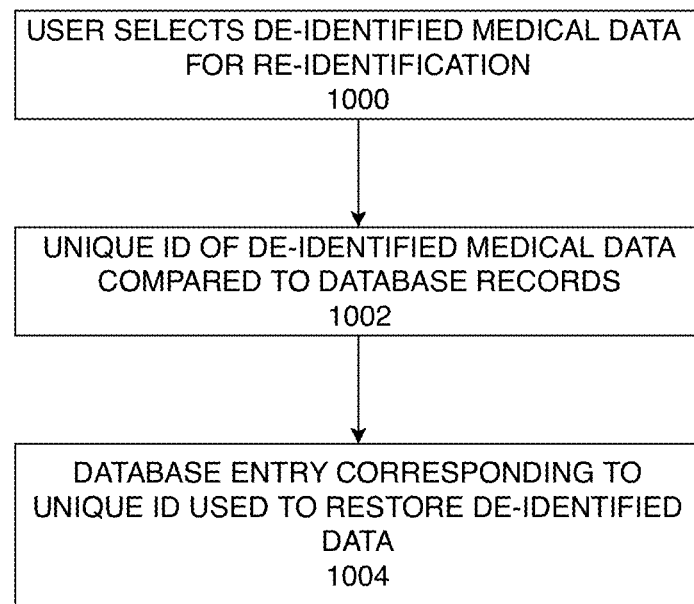
FIG. 10 is a flowchart illustrating the steps of re-identifying medical data, according to an embodiment of the invention.

At step 316, the parseable document is parsed for DICOM metadata. In an embodiment, the DICOM metadata, such as DICOM tags, can be selected for the purposes of de-identification so that the de-identification complies with § 161.514(b)(2) and § 161.514(c) of the HIPAA Privacy Rule. FIG. 10 described herein is an exemplary list of DICOM metadata that may be utilized for de-identification. In another embodiment, the user, recipient 112, data provider 100, and/or institution 106 can configure the specific tags to be sanitized by the de-identification process.

At step 318, the DICOM metadata are sanitized by the sanitizing engine 104. In an embodiment, the sanitizing engine 104 fills the DICOM metadata fields with randomly generated characters. The sanitizing engine 104 utilizes an algorithm or script to generate the random characters such that the random characters have no relation to the underlying patient, patient data, PHI, PII, or information that existed in the header data or medical data prior to the de-identification process.

In another embodiment, the DICOM metadata fields are cleared so that they are empty, or they are blacked out with a black shape, such as a polygon, rectangle, circle, square, free-form, and the like.

In yet another embodiment, the sanitizing engine 104 utilizes an algorithm or script to generate a specific string of replacement characters. For example, if a recipient, such as a customer, can provide specific instructions of how information in DICOM metadata should be replaced or restructured. For example, a recipient 112 may request that the "patient ID" metadata field is replaced with a string in a certain format based on where the medical data originated. In an illustrative, non-limiting example, the first three digits of the original "patient ID" is replaced with "001" to indicate a first provider, or replaced with "002" to indicate a second provider.

Thus, a recipient 112 can provide instructions or a template on how certain or all DICOM metadata fields should be replaced, restructured, and/or appended. In an embodiment, a recipient 112 can create different templates based on diagnostic modalities, imaging locations, imaging equipment, imaging procedures, and the like.

At step 320, the medical report text is analyzed to identify instance of PHI, and the identified PHI is sanitized by the sanitizing engine 104. In an embodiment, the sanitizing engine 104 replaces the PHI in the medical report text with randomly generated characters. The sanitizing engine 104 utilizes an algorithm or script to generate the random characters such that the random characters have no relation to the underlying patient, patient data, or information that existed in the header data or medical data prior to the de-identification process. In an embodiment, the sanitizing engine 104 may utilize natural language processing to identify instances of PHI.

Furthermore, the sanitizing engine 104 can use regular expression mechanisms (also known as RegEx, RegExp, or R.E.) to identify and sanitize characters and text. For example, regular expression can be used to identify and sanitize initials, geographic location coordinates, text fragments, and the like.

In another embodiment, the sanitizing engine 104 can analyze sanitized medical reports over time using machine learning to more efficiently and quickly identify instances of PHI on future medical reports.

In another embodiment, the PHI is cleared so that the underlying field where the PHI is located is empty, or the PHI is blacked out with black rectangles.

Figure 4:
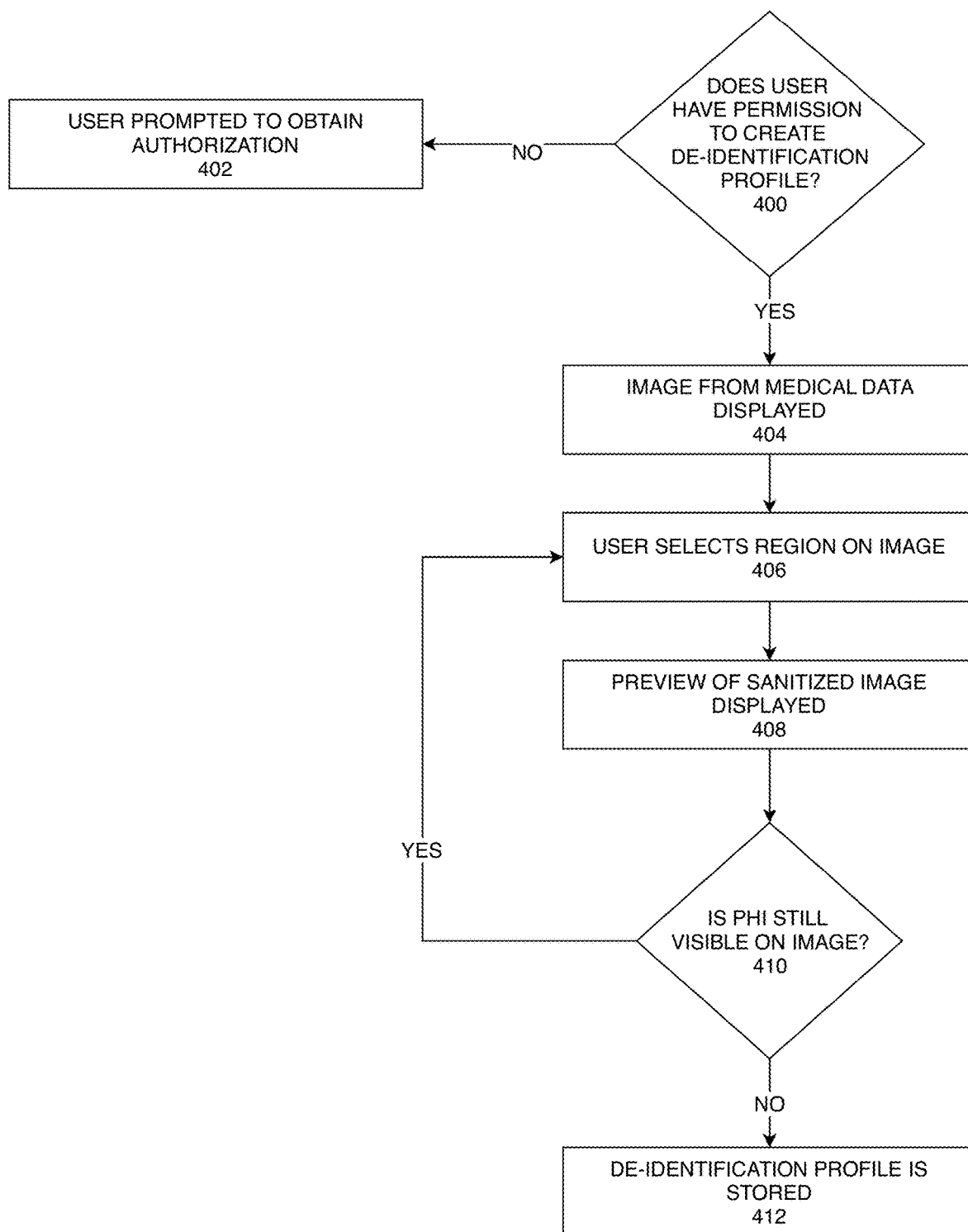
FIG. 4 is a flowchart illustrating the steps of creating a de-identification profile for a diagnostic modality, according to an embodiment of the invention.

FIG. 4 is a flowchart illustrating the steps of creating a de-identification profile for a diagnostic modality, according to an embodiment of the invention. In an embodiment, pre-defined de-identification profiles can be generated for different diagnostic modalities, imaging locations, imaging equipment, imaging procedures, and the like. The de-identification profiles allow known, standard, or common areas that contain PHI on a diagnostic image to be defined for a specific diagnostic modality, such that a blackout zone or sanitizing process can be applied to such areas on any diagnostic image that matches the de-identification profile (i.e., any diagnostic image that, for example, is generated using the specific modality that the de-identification profile was created for).

At step 400, the data provider 100 determines if the user has permission to create a de-identification profile for a diagnostic modality. In an embodiment, only authorized users can create a de-identification profile, and the authorization is designated by an administrator affiliated with the data provider 100 or institution 106. If the user does not have permission, the process continues to step 402, where the user is prompted to obtain authorization.

If, however, the user has permission to create a de-identification profile, then at step 404, a dialogue window is displayed to the user, where the dialogue window includes a diagnostic image from one of the selected medical data. At step 406, the user is prompted to select portions of the diagnostic image containing PHI using a selection tool. The selection tool can take various shapes, and in an embodiment, can be a rectangular selection tool.

In other embodiments, the selection tool can be free form, or take various shapes such as elliptical, circular, column, row, square, a lasso and the like. In another embodiment, the selection tool can be a magnetic lasso tool which follows lines and outlines like a magnet, and facilitates the selection of PHI areas having contours.

In an embodiment, the user can manipulate the size and dimensions of the selection tool, so that a larger or smaller area of the diagnostic image can be selected.

In an embodiment, the selection tool can further be a magic wand tool which facilitates the selection of a specific color in an area with contrasting colors. For example, the magic wand tool allows for an entire PHI area which may have a white background to be selected where the remaining non-PHI areas of the diagnostic image are black. Similarly, the selection tool can have an inverse feature where the inverse color is automatically selected. For example, the inverse feature allows for all non-black areas to be selected by the user.

At step 408, all selected portions are sanitized from the diagnostic image, such as by masking with a blackout zone, in order to generate a preview of the sanitized diagnostic image for the user. In another embodiment, the selected portions are deleted, blurred, obfuscated, cropped, or otherwise made illegible. In yet another embodiment, any pixels, characters, or text in the selected portions are replaced with randomly generated characters. In this embodiment, the sanitizing engine 104 utilizes an algorithm or script to generate the random characters such that the random characters have no relation to the underlying patient, patient data, medical data, or information that existed on the diagnostic image prior to the de-identification process.

In another embodiment, the user can be prompted at step 406 to select portions of the diagnostic image that do not contain PHI. In this embodiment, at step 408, all non-selected portions are sanitized from the diagnostic image in order to generate a preview of the sanitized diagnostic image for the user.

At step 410, once the diagnostic image has been sanitized, the user can be prompted to confirm that no additional PHI remains visible on the diagnostic image. If PHI remains visible, the process returns to step 406 where the user can again select areas with PHI to be sanitized.

If no PHI remains visible, then the process continues to step 412 where the de-identification profile is saved to the data provider 100 or virtual machine 116 for subsequent retrieval when a medical data matching the de-identification profile is selected for sanitizing.

In an embodiment, the modality information, equipment manufacturer, station information, and respective location information is saved to the data provider 100 or virtual machine 116. In addition, the dimensions of the diagnostic image used to generate the de-identification profile is stored so the data provider 100 can determine if future images to-be sanitized are appropriate candidates for the de-identification profile. For example, the dimensions can include the size (in, for example, pixels, inches, centimeters, etc.) of the diagnostic image, an aspect ratio of the diagnostic image, and/or a resolution of the diagnostic image. In another embodiments, properties such as the quality, compression, amount of loss, and the like, can also be stored.

In yet another embodiment, the de-identification profile can be automatically generated, using for example, machine learning. For example, previously generated de-identification profiles can be analyzed based on accuracy over time, in order to generate future de-identification profiles based on historical sanitization success or failure results.

Figure 5:
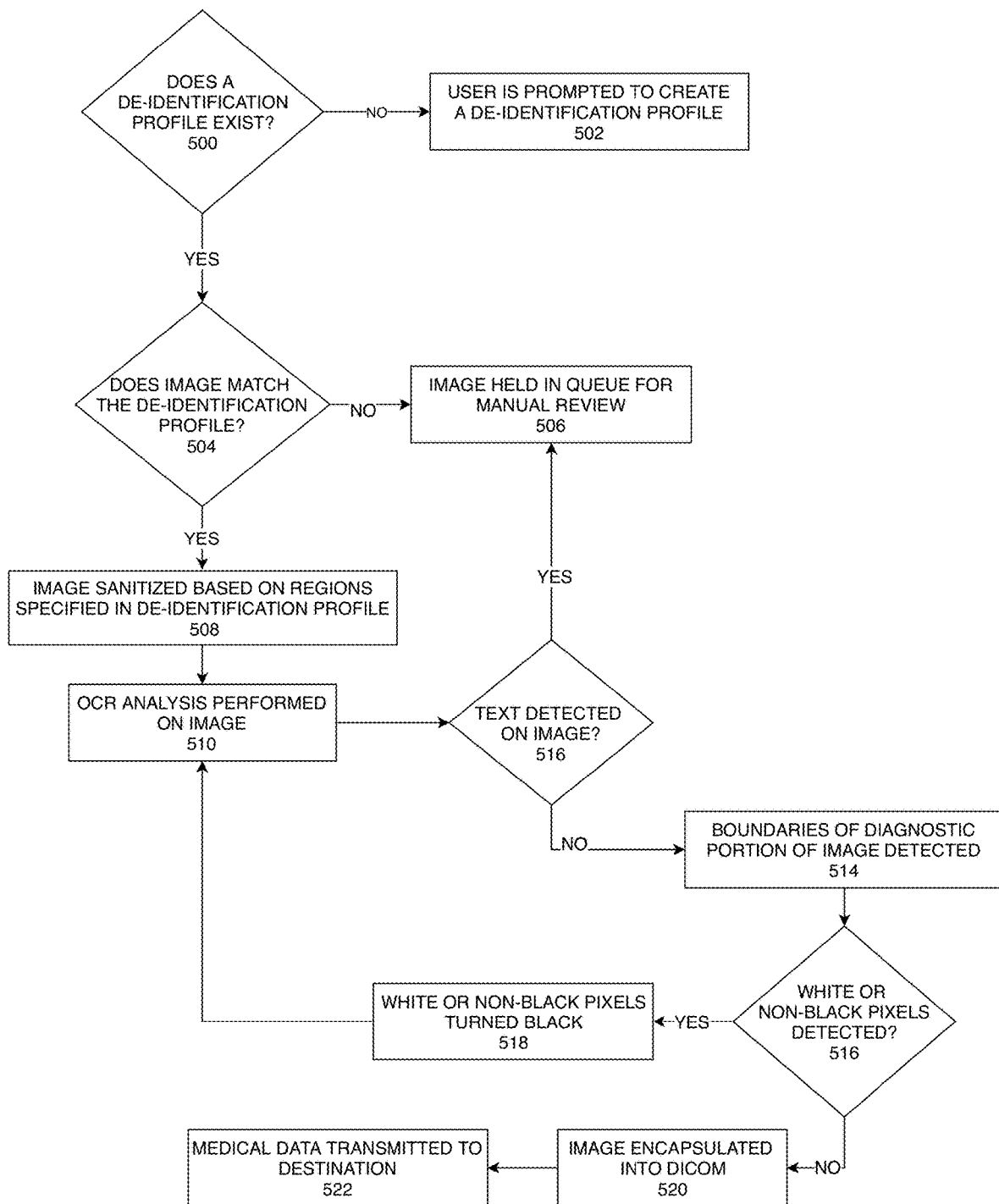
FIG. 5 is a flowchart illustrating the steps of de-identifying burned in PHI on diagnostic images, according to an embodiment of the invention.

FIG. 5 is a flowchart illustrating the steps of de-identifying burned in PHI on diagnostic images, according to an embodiment of the invention. At step 500, the data provider 100 determines is a de-identification profile exists for a modality that produced a diagnostic image within a selected medical data. In an embodiment, the data provider 100 compares various DICOM metadata contained in the diagnostic image, such as, for example, the modality, equipment manufacturer, station information, and other station or equipment-based tags, or pre-defined user tags.

If the DICOM metadata on the diagnostic image do not match an existing de-identification profile, then the user is promoted to create a de-identification profile at step 502, and the process returns to step 400 as shown in FIG. 4.

If, however, the DICOM metadata on the diagnostic image match an existing de-identification profile, then the process continues to step 504 where the size of the diagnostic image is compared to the image size specified in the de-identification profile. In an embodiment, instead of, or in addition to the comparison of size, the properties of the diagnostic image, such as its aspect ratio, resolution, quality, amount of loss, and the like can compared against the properties stored in the de-identification profile.

In an embodiment, the comparison can be based on a threshold value, where the sanitizing engine 104 determines if a selected diagnostic image is within a certain threshold of the size or properties of the de-identification profile. The threshold value can be manually determined, or can be determined by the data provider 100 or sanitizing engine 104 over time using machine learning, based on analysis of prior sanitizing results using de-identification profiles.

If, however, the diagnostic image does not match, or is not within an acceptable threshold value of, the size and/or properties in the de-identification profile, then the process continues to step 506 where the diagnostic image is held in a queue for manual review. In an embodiment, the process can return to step 400 as shown in FIG. 4, where the user is prompted to create a new de-identification profile.

If the diagnostic image matches, or is within an acceptable threshold value of, the size and/or properties in the de-identification profile, then at step 508, blackout zones are automatically applied to the diagnostic image at the area(s) specified in the de-identification profile. In another embodiment, the area(s) specified in the de-identification profile are deleted, blurred, obfuscated, cropped, or otherwise made illegible instead of, or in addition to, being applied with a blackout zone.

In another embodiment, if there are multiple areas of a diagnostic image specified in the de-identification profile to be sanitized, the user can be prompted to review each area prior to the processing by the sanitizing engine 104. For example, the user can approve or reject a sanitizing operation of an area specified in the de-identification profile based on if there is actual PHI present on a specific diagnostic image, or if a diagnostic portion of the image is located in the specified area(s).

Next, at step 510, a first stage of quality control is performed by the sanitizing engine 104 where optical character recognition (OCR) is performed on a portion of, or the entire, diagnostic image, after the blackout zones have been applied. At step 512, the sanitizing engine 104 analyzes the diagnostic image after the OCR process to determine if any text or characters remain on the diagnostic image.

In an embodiment, the sanitizing engine 104 only analyzes the areas specified in the de-identification profile that contain PHI to determine if any pixels, text or characters (collectively, "pixels") still remain. If pixels are identified in these areas, then the sanitizing operation performed in step 508 is deemed to have failed. In this embodiment, the OCR operation is only be performed on the area specified in the de-identification profile, and where the blackout zone or sanitizing process has been applied, and not on the entire diagnostic image.

In another embodiment, the sanitizing engine 104 analyzes the entire diagnostic image, and not only the areas specified in the de-identification profile. In this embodiment, the OCR operation can be performed on the entire diagnostic image, and is not limited to any areas of the diagnostic image, or just where the blackout zone or sanitizing process has been applied.

If any pixels are identified in the diagnostic image after the OCR operation, then the process continues back to step 506, where the diagnostic image is held in a queue for manual review. The user can be prompted to review the diagnostic image and compare it to the de-identification profile to determine if the any aspect of the diagnostic modality that created that specific diagnostic image may have changed, resulting in the de-identification profile to no longer be accurate or applicable.

If, however, no pixels are identified in the diagnostic image after the OCR operation, then at step 514, a second stage of quality control is performed by the sanitizing engine 104 using an image analysis technique. In an embodiment, the image analysis is used to detect a gradient boundary (i.e., a directional change in the intensity or color in an image) on the diagnostic image in order to determine where the actual diagnostic portion of the image ends. The diagnostic portion can be referred to the region of interest in the diagnostic image, and the gradient boundary identifies the bounds of the region of interest. Step 514 is an optional step, and is not mandatory.

At step 516, the sanitizing engine 104 determines if any white or non-black pixels exist outside of the region of interest. If any white or non-black pixels are identified outside of the region of interest, then at step 518, these pixels are converted, masked, or turned black by the sanitizing engine 104. In another embodiment, these pixels are deleted, blurred, obfuscated, cropped, or otherwise made illegible. The process then returns to step 510, where an OCR operation is performed on the diagnostic image again. Step 516 is an optional step, and is not mandatory.

If, however, no white or non-black pixels are identified outside of the region of interest, then at step 520, the sanitized parseable document and sanitized JPEG image are re-encapsulated back into the DICOM format by the data provider 100 or the sanitizing engine 104. The DICOM re-encapsulated file is now sanitized of any PHI, and is ready to be transmitted to third-party recipients at step 522. The third-party recipients can be internal or external to the data provider 100, or institution being serviced by the data provider 100.

Figure 6A:
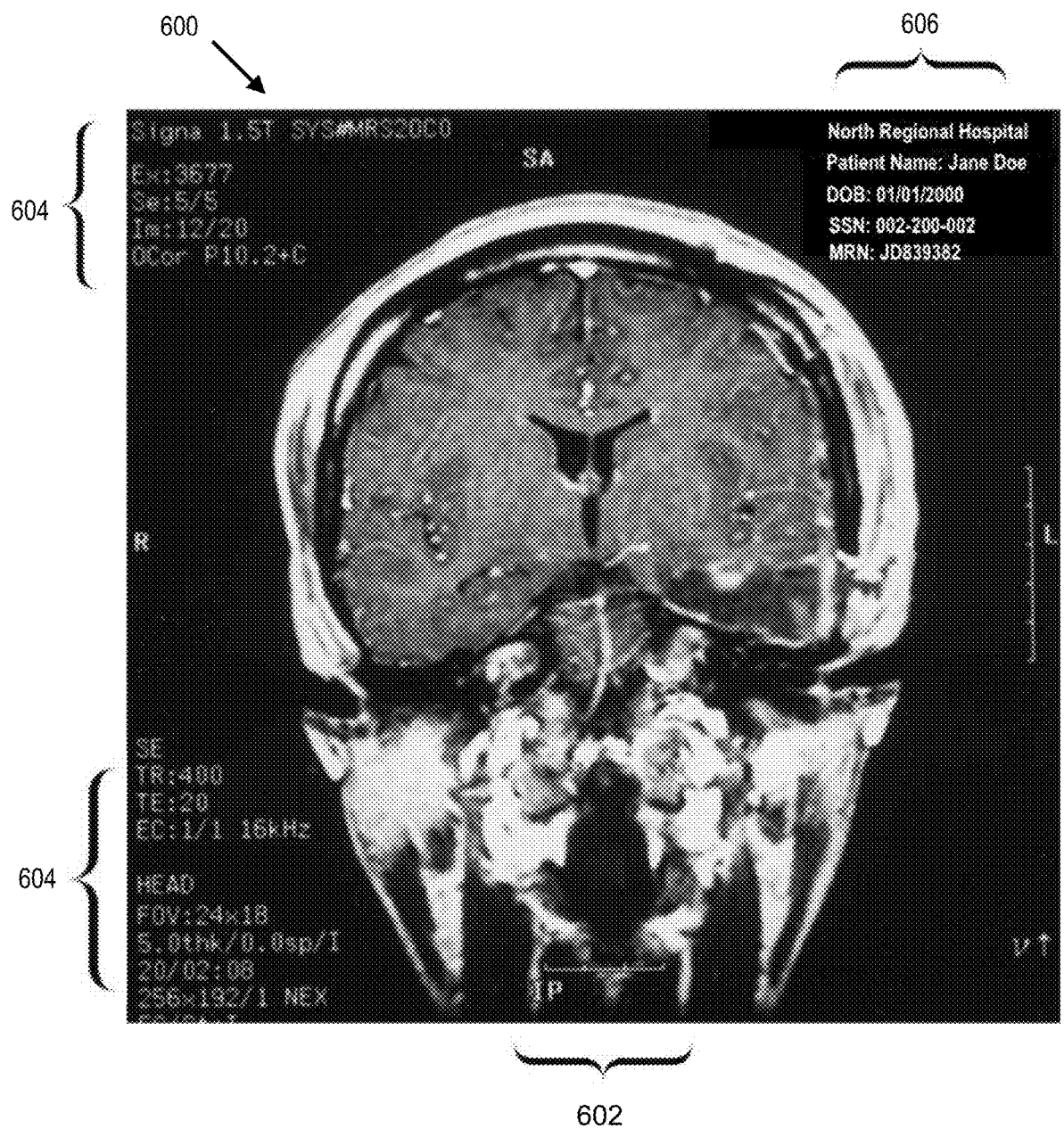
FIG. 6A is view of a diagnostic image prior to being de-identified, according to an embodiment of the invention.

FIG. 6A is view of a diagnostic image prior to being de-identified, according to an embodiment of the invention. The diagnostic image 600 includes a diagnostic portion 602, also referred to as the region of interest, as well as non-PHI areas 604 and PHI area 606. FIG. 6A is an exemplary diagnostic image 600, and the invention is not limited to any specific modality, and the diagnostic image can include multiple PHI areas at various other locations on the diagnostic image, as well as multiple non-PHI areas at various other locations on the diagnostic image.

In an embodiment, the PHI area 606 includes personally identifiable information, such as a patient's name, date of birth, social security number, accession numbers, and medical record number. In addition, the PHI area can further include location and site information, such as the institution name, referring physician name, and the like.

In an embodiment, the non-PHI areas 604 include equipment, modality, scan, and/or image specific information, such as the type of scan/modality, image dimensions, slice thickness, echo time, the number of phase encoding steps, repetition time, body part, equipment manufacturer, and the like.

Figure 6B:
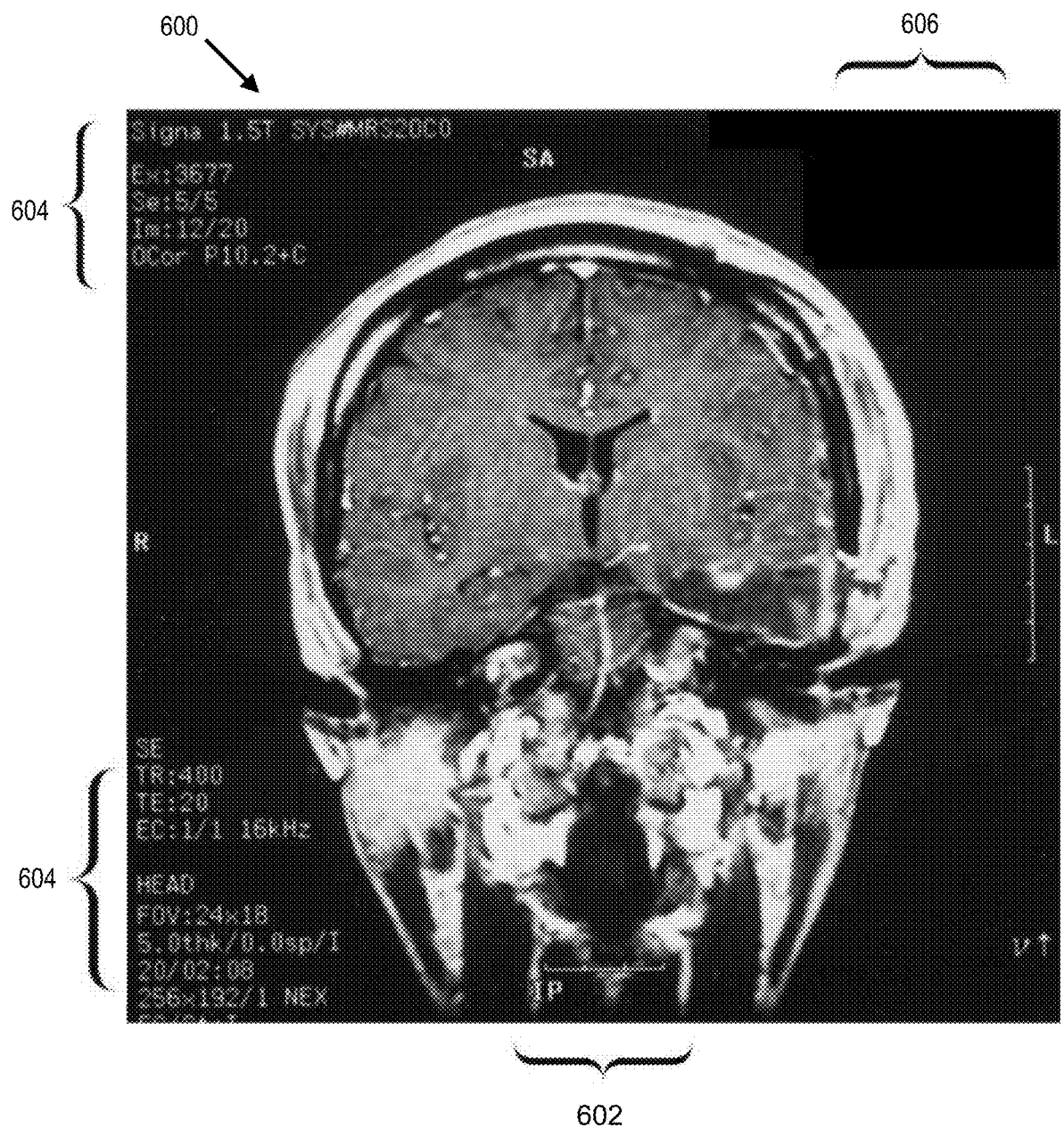
FIG. 6B is a view of a diagnostic image after being de-identified, according to an embodiment of the invention.

FIG. 6B is a view of a diagnostic image after being de-identified, according to an embodiment of the invention. As shown in FIG. 6B, PHI area 606 is blacked out with a blackout zone, such that the PHI shown in FIG. 6A is no longer visible. However, the non-PHI areas 604 remain visible to the user.

Figure 7A:
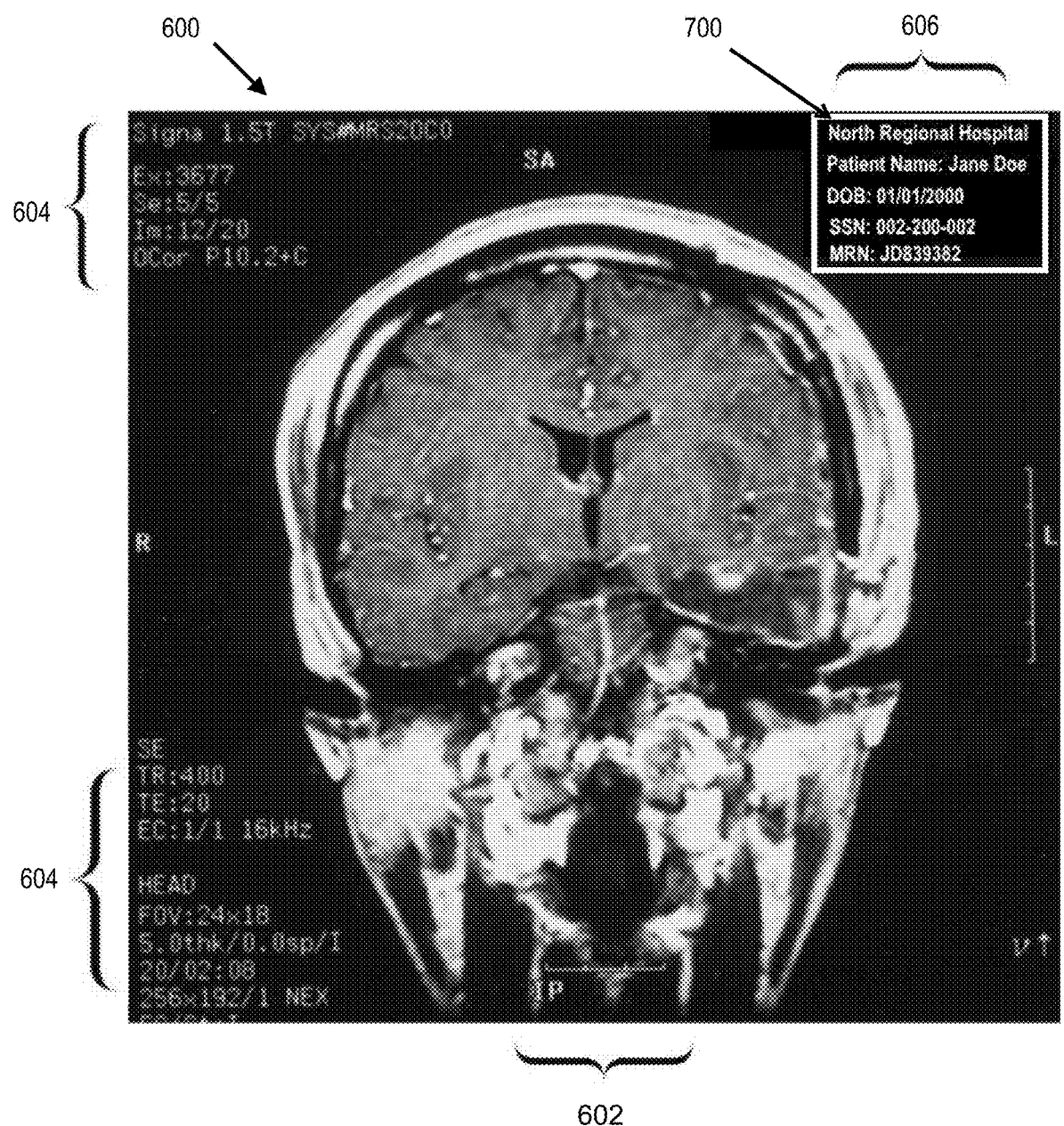
FIG. 7A is a view of a dialogue window with a selection tool used to select PHI regions to create a de-identification profile, according to an embodiment of the invention.

FIG. 7A is a view of a dialogue window with a selection tool used to select PHI areas to create a de-identification profile, according to an embodiment of the invention. In an embodiment, the user utilizes a selection tool 700 to select areas of the diagnostic image 600 that contains PHI, after the diagnostic image has undergone an OCR process, as described above. The selection too 700 can be operated by an input device such as a mouse, trackball, touchpad, pointing stick, or a touchscreen. In another embodiment, the user can manipulate the selection tool 700 using gestures either via touching a touchscreen, or which are transmitted via a user's wearable device to the user's computing device on which the dialogue window is displayed.

In an embodiment, the selection tool 700 is used to isolate a PHI area 606. Once the selection tool 700 is confirmed on the diagnostic image 600, the sanitizing engine 104 generates a preview of the sanitized diagnostic image for the user, such as by masking the area bounded by the selection tool 700 with a blackout zone. In another embodiment, the area bounded by the selection tool 700 can be deleted, blurred, obfuscated, cropped, or otherwise made illegible. In yet another embodiment, any pixels, characters, or text within the area bounded by the selection tool 700 can be replaced with randomly generated characters. In this embodiment, the sanitizing engine 104 utilizes an algorithm or script to generate the random characters such that the random characters have no relation to the underlying patient, patient data, medical data, or information that existed on the diagnostic image prior to the de-identification process.

Figure 7B:
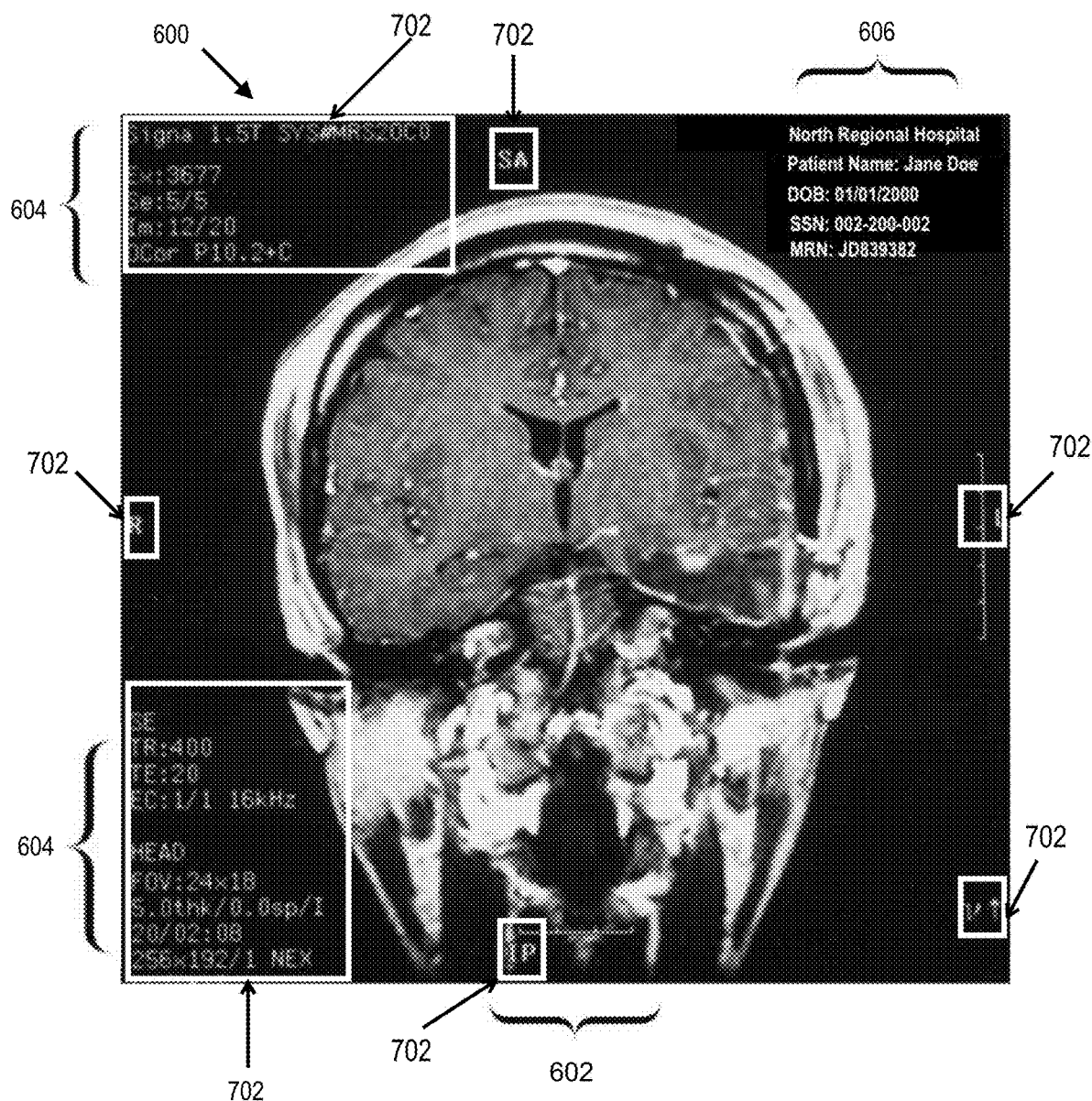
FIG. 7B is a view of a dialogue window with a selection tool used to select non-PHI regions to create a de-identification profile, according to an embodiment of the invention.

FIG. 7B is a view of a dialogue window with a selection tool used to select non-PHI areas to create a de-identification profile, according to an embodiment of the invention. In an embodiment, instead of selecting PHI areas, user utilizes a selection tool 702 to select areas of the diagnostic image 600 that do not contain PHI, after the diagnostic image has undergone an OCR process, as described above. Referring to FIG. 7B, the selection tool 702 has been applied to various non-PHI areas, including non-PHI areas 604.

Once the selection tool 702 is confirmed on the diagnostic image 600, the sanitizing engine 104 generates a preview of the sanitized diagnostic image for the user, such as by masking any pixels, characters, or text not within the regions bounded by the selection tool 700 with a blackout zone. In another embodiment, any pixels, characters, or text not within the regions bounded by the selection tool 702 are deleted, blurred, obfuscated, cropped, or otherwise made illegible. In yet another embodiment, any pixels, characters or text not within the area bounded by the selection tool 702 are replaced with randomly generated characters. In this embodiment, the sanitizing engine 104 utilizes an algorithm or script to generate the random characters such that the random characters have no relation to the underlying patient, patient data, medical data, or information that existed on the diagnostic image prior to the de-identification process.

Figure 8:
FIG. 8 is a view of a region of interest identified by image analysis, according to an embodiment of the invention.

FIG. 8 is a view of a region of interest identified by image analysis, according to an embodiment of the invention. In an embodiment, after the first stage of quality control is performed by the sanitizing engine 104, a second stage of quality control is performed by the sanitizing engine 104 using an image analysis technique. the image analysis is used to detect a gradient boundary 800 (i.e., a directional change in the intensity or color in an image) on the diagnostic image in order to determine where the actual diagnostic portion 802 of the image ends. The diagnostic portion 802 can be referred to the region of interest in the diagnostic image, and the gradient boundary 800 identifies the bounds of the region of interest.

Once the gradient boundary 800 is confirmed on the diagnostic image 600, the sanitizing engine 104 generates a preview of the sanitized diagnostic image for the user, such as by masking any pixels outside of the gradient boundary 800 a blackout zone. In another embodiment, any pixels outside of the gradient boundary 800 can be deleted, blurred, obfuscated, cropped, or otherwise made illegible. In yet another embodiment, any pixels, characters, or text outside of the gradient boundary 800 can be replaced with randomly generated characters. In this embodiment, the sanitizing engine 104 utilizes an algorithm or script to generate the random characters such that the random characters have no relation to the underlying patient, patient data, medical data, or information that existed on the diagnostic image prior to the de-identification process.

FIG. 9 is a table with exemplary DICOM metadata, according to an embodiment of the invention. The DICOM metadata, also referred to as DICOM tags, are DICOM data elements, or attributes, which are usually in the format (XXXX,XXXX) with hexadecimal numbers, and which may be divided further into DICOM group numbers (not shown) and DICOM element numbers (not shown). In addition, a DICOM value representation (VR) that describes the data type and format of the attribute value can also be associated with each DICOM tag (not shown).

In a preferred embodiment, the DICOM tags shown in FIG. 9 are utilized for the purposes of de-identification, however the tags shown in FIG. 9 are exemplary, and the invention is not limited to these specific tags being used for de-identification. For example, a user can configure specific DICOM tags to be utilized for de-identification. In an embodiment, sanitization of the DICOM tags referred to in FIG. 9 are preferred as they most comply with § 161.514 (b)(2) and § 161.514(c) of the HIPAA Privacy Rule.

FIG. 10 is a flowchart illustrating the steps of re-identifying medical data, according to an embodiment of the invention. At step 1000, the user selects a de-identified medical data to re-identify. In an embodiment, the user can be any entity or individual that has been granted the ability to re-identify de-identified medical data, either by the institution 106, the data provider 100, the recipient 112.

In an embodiment, re-identification may only be permitted if informed consent has been provided by the patient. In another embodiment, re-identification requires an additional payment or surcharge. In yet another embodiment, re-identified medical data may include security features such that it cannot be transmitted externally, printed, screenshot, or otherwise modified, shared, or disseminated.

At step 1002, the unique identification string, such as the SOP instance UID, associated with the selected medical data at step 314 described above is retrieved. The unique identification string is compared to medical records stored in the database 114.

At step 1004, the data entry corresponding to the unique identification string is identified in the database 114, and the header data and/or parseable document is retrieved using the unique identification string as a key. Once the header data and/or parseable document is retrieved, the de-identified medical data is re-identified using the information located in the header data and/or parseable document.

In an embodiment, if the medical data was purchased or obtained by the user via the medical data marketplace 118, then the medical data may not be eligible for re-identification.

While the principles of the disclosure have been illustrated in relation to the exemplary embodiments shown herein, the principles of the disclosure are not limited thereto and include any modification, variation or permutation thereof.

The invention claimed is:

1. A system for providing a medical data marketplace, the system comprising:
   a database storing a plurality of de-identified medical data sets, wherein each de-identified medical data set is owned by a different data owner;
   a server coupled to the database; and
   a computer-readable storage medium operably connected to a processor coupled to the server, the computer-readable storage medium containing programming instructions that, when executed, cause the processor to:
   generate an interface that allows a customer to submit a search request that includes at least one criteria, wherein the criteria is selected from a group consisting of a modality type, an equipment manufacturer, a body part, a study description, a protocol name, a requested procedure description, a scheduled procedure step description, and a keyword,
receive the search request from the interface,
query the database using the criteria to retrieve at least one matching medical data set from the plurality of de-identified medical data sets,
display the at least one matching medical data set on the interface, and
facilitate a financial transaction related to the at least one matching medical data set between a respective data owner and the customer,
wherein the financial transaction is stored on a blockchain communicatively coupled to the server.

2. The system of claim 1, wherein the at least one matching medical data set is not eligible for re-identification after the financial transaction is conducted.

3. The system of claim 1, wherein the criteria is a study date or a study date range.

4. The system of claim 1, wherein the criteria is a geographic criteria or a demographic criteria.

5. The system of claim 1, wherein the financial transaction is a sale of the at least one matching medical data set.

6. The system of claim 1, wherein the financial transaction is a license to the at least one matching medical data set.

7. The system of claim 1, wherein the server and the respective data owner share proceeds from the financial transaction.

8. The system of claim 1, wherein the server receives a membership fee from the customer.

9. The system of claim 1, wherein each of the plurality of medical data sets include a medical report and at least one diagnostic image.

10. A system for providing a medical data marketplace, the system comprising:
a database storing a plurality of diagnostic image sets, wherein each diagnostic image set is owned by a different data owner;
a server coupled to the database; and
a computer-readable storage medium operably connected to a processor coupled to the server, the computer-readable storage medium containing programming instructions that, when executed, cause the processor to:
perform a de-identification process on each of the plurality of diagnostic image sets to generate a plurality of de-identified diagnostic image sets,
generate an interface that allows a customer to submit a search request that includes at least one criteria, wherein the criteria is selected from a group consisting of a modality type, an equipment manufacturer, a body part, a study description, a protocol name, a requested procedure description, a scheduled procedure step description, and a keyword,
receive the search request from the interface,
query the database using the criteria to retrieve at least one matching diagnostic image set from the plurality of de-identified diagnostic image sets,
display the at least one matching diagnostic image set on the interface, and
offer for sale to the customer the at least one matching diagnostic image set as an auction via the interface.

11. The system of claim 10, wherein the at least one matching diagnostic image set is not eligible for re-identification after the financial transaction is conducted.

12. The system of claim 10, wherein the criteria is a study date or a study date range.

13. The system of claim 10, wherein the criteria is a geographic criteria or a demographic criteria.

14. The system of claim 10, wherein the financial transaction is a sale of the at least one matching diagnostic image set.

15. The system of claim 10, wherein the financial transaction is a licensing of the at least one matching diagnostic image set.

16. The system of claim 10, wherein the server receives a listing fee from each of the different data owners.

17. The system of claim 10, wherein at least one of the server and the respective data owner share proceeds from the financial transaction.

18. A system for providing a medical data marketplace, the system comprising:
a database storing a plurality of medical data sets, wherein each medical data set is owned by a different data owner;
a server coupled to the database; and
a computer-readable storage medium operably connected to a processor coupled to the server, the computer-readable storage medium containing programming instructions that, when executed, cause the processor to:
perform a de-identification process on each of the plurality of medical data sets to generate a plurality of de-identified medical data sets,
generate an interface that allows a customer to submit a request for a bulk set of de-identified medical data,
randomly select at least one de-identified medical data set from the plurality of de-identified medical data sets, and
facilitate a financial transaction related to the randomly selected at least one de-identified medical data set between a respective data owner and the customer,
wherein the de-identification process includes the steps of:
retrieving, by the server, a medical image from a medical data set from the plurality of medical data sets;
determining, by the server, a modality associated with the medical image;
retrieving, by the server, a de-identification profile for the modality, wherein the de-identification profile specifies at least one area of the medical image that contains patient information; and
applying, by a sanitizing engine coupled to the server, a blackout zone over the area of the medical image specified in the de-identification profile, wherein the patient information within the blackout zone is deleted by the sanitizing engine.

* * * * *